(12) United States Patent
Madsen et al.

(10) Patent No.: US 6,238,343 B1
(45) Date of Patent: May 29, 2001

(54) QUALITY ASSURANCE ULTRASOUND PHANTOMS

(75) Inventors: Ernest L. Madsen; Gary R. Frank, both of Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 0 days.

(21) Appl. No.: 09/340,631

(22) Filed: Jun. 28, 1999

(51) Int. Cl.[7] .................................................. A61B 8/00

(52) U.S. Cl. ................................ 600/437; 73/10 V (58) Field of Search .................... 73/625–629, 866.4, 73/865.6, 618, 619, 1.86; 600/437, 449; 434/268

(56) References Cited

U.S. PATENT DOCUMENTS

| | | |
|---|---|---|
| 4,116,040 | 9/1978 | Skoknecht et al. . |
| 4,277,367 | 7/1981 | Madsen et al. . |
| 4,286,455 | 9/1981 | Ophir et al. . |
| 4,331,021 | 5/1982 | Lopez et al. . |
| 4,406,153 | 9/1983 | Ophir et al. . |
| 4,417,582 | 11/1983 | Trimmer et al. . |
| 4,453,408 | 6/1984 | Clayman . |
| 4,843,866 | 7/1989 | Madsen et al. . |
| 4,894,013 * | 1/1990 | Smith et al. ............... 434/628 |
| 5,054,310 | 10/1991 | Flynn . |
| 5,312,755 | 5/1994 | Madsen et al. . |
| 5,574,212 | 11/1996 | Madsen et al. . |
| 5,625,137 | 4/1997 | Madsen et al. . |
| 5,649,538 * | 7/1997 | Langton ..................... 600/449 |
| 5,670,719 | 9/1997 | Madsen et al. . |
| 5,756,875 * | 5/1998 | Parker et al. ............... 73/1 DV |
| 5,827,942 | 10/1998 | Madsen et al. . |
| 5,935,073 * | 8/1999 | Wilson et al. .............. 600/449 |

FOREIGN PATENT DOCUMENTS 28-14-336    5/1979  (DE) .

OTHER PUBLICATIONS

Goldstein, et al., "Particle Image–Resolution Test Object," J. Ultrasound Med., vol. 2, May (1983), pp. 195–209.
Smith, S.W. and H. Lopez, "A Contrast–Detail Analysis of Diagnostic Ultrasound Imaging," Med. Phys., vol. 9, No. 1, pp. 4–12, Jan./Feb. 1982.
Carson, Paul L., "What a Hospital Physicist Needs in a Transducer Characterization Standard: Are Tissue Equivalent Test Objects Necessary?" IEEE Transactions on Sonics and Ultrasonics, vol. S U–26, No. 1, Jan. 1979, pp. 1–6.
Smith, et al., "Frequency Independent Ultrasound Contrast–Detail Analysis," Ultrasound in Med. & Biol., vol. 11, No. 3, pp. 467–477, May/Jun. 1985.
New Product Announcement, The Wisconsin Spherical Void Phantom, Oct. 1988.
Model 44 Specifications, publication date unknown, but 1998 or earlier.

* cited by examiner

Primary Examiner—Marvin M. Lateef
Assistant Examiner—Ali M. Imam
(74) Attorney, Agent, or Firm—Foley & Lardner (57) ABSTRACT

An ultrasound phantom is adapted to provide multiple testing capabilities for quality assurance on ultrasound scanners. The phantom includes a section with an array of target spheres which allow the ability of the scanner to delineate the intersection of a plane of symmetry of the scan slice with diagnostic objects to be determined. Other sections allow low contrast resolution of large objects, spatial resolution regarding lateral and axial dimensions, maximum visualization depth, image gray level uniformity, and distance measurement accuracy to be determined. The phantom may be utilized to provide comparative tests of various scanners and to monitor the performance of a particular scanner over time to determine any changes in the performance of the scanner.

36 Claims, 5 Drawing Sheets

QUALITY ASSURANCE ULTRASOUND PHANTOMS

This invention was made with United States government support warded by the following agency: NIH CA39224. The United States government has certain rights in this invention.

FIELD OF THE INVENTION

This invention pertains generally to the field of ultrasound phantoms for use with ultrasound scanners.

BACKGROUND OF THE INVENTION

Materials which closely mimic the ultrasonic propagation characteristics of human tissue are employed in imaging phantoms and other test objects for use with ultrasound scanners. These phantoms may be used to carry out performance checks on ultrasound scanners. Phantoms may also be used for training or testing student technologists in the operation of ultrasound scanners or the interpretation of ultrasound images produced by such scanners.

Ideally, such material should be capable of mimicking soft human tissue with respect to at least three characteristics: speed of sound, ultrasonic attenuation, and ultrasonic backscattering. Additionally, the attenuation coefficient should be approximately proportional to the ultrasonic frequency. In other words, the variation of the attenuation coefficient with respect to frequency, or the attenuation coefficient slope, should remain constant for varying ultrasonic frequencies. The attenuation coefficient should extrapolate to nearly zero as the frequency reduces to zero. These characteristics of human tissue should be maintained at all frequencies in the typical range of ultrasonic scanners, from 1–10 MHz. Moreover, the variation of these characteristics within the range of room temperature should be small. Additionally, these materials should be stable in time and invulnerable to reasonable environmental fluctuations. They should also be free of any pockets of air or gas. Furthermore, the bulk properties of the material should be the same throughout the volume of a particular phantom or phantom section.

A tissue mimicking material satisfying the above characteristics was disclosed in U.S. Pat. No. 4,277,367, to Madsen, et al., entitled Phantom Material and Methods in which both the speed of sound and the ultrasonic attenuation properties could be simultaneously controlled in a mimicking material based on water based gels, such as those derived from animal hides. In one embodiment, ultrasound phantoms embodying the desired features for mimicking soft tissue were prepared from a mixture of gelatin, water, n-propanol and graphite powder, with a preservative. In another embodiment, an oil and gelatin mixture formed the basis of the tissue mimicking material.

Tissue mimicking material is typically used to form the body of an ultrasound scanner phantom. This is accomplished by enclosing the material in a container which is closed by an ultrasound transmitting window cover. The tissue mimicking material is admitted to the container in such a way as to exclude air bubbles from forming in the container. In addition to the tissue mimicking material itself, scattering particles, spaced sufficiently close to each other that an ultrasound scanner is incapable of resolving individual scattering particles, and testing spheres or other targets may be located within the phantom container, suspended in the tissue mimicking material body. Such an ultrasound phantom is useful in evaluating the ability of ultrasound medical diagnostic scanners to resolve target objects of selected sizes located throughout the tissue mimicking material. The objective is for the ultrasound scanner to resolve the testing spheres or other targets from the background material and scattering particles. This type of ultrasound phantom is described in U.S. Pat. No. 4,843,866, to Madsen, et al., entitled Ultrasound Phantom.

U.S. Pat. No. 5,625,137 to Madsen, et al. discloses a tissue mimicking material with intrinsic very low acoustic backscatter coefficient that may be in liquid or solid form. A component in both the liquid and solid forms is a filtered aqueous mixture of large organic water soluble molecules and an emulsion of fatty acid esters, which may be based on a combination of milk and water. Hydroxy compounds, such as n-propanol, can be used to control the ultrasonic speed of propagation through the material and a preservative from bacterial invasion can also be included. The use of scattering particles allows a very broad range of relative backscatter levels to be achieved.

Ultrasound scanners for medical imaging are available from several manufacturers, and in various models, with corresponding variations in the performance of the scanners. There are several performance characteristics of ultrasound scanners that affect the ability of the scanner to provide useful information to medical personnel. One characteristic is the ability of the scanner to delineate the intersection of the plane of symmetry of the scan slice with the three-dimensional boundary of an object regardless of its shape, which is important in the ability of the scanner to provide morphological information concerning diagnostic targets such as tumors. The scanner should also be able to provide contrast resolution of large objects, such as large tumors, which have relatively low ultrasound contrast with respect to surrounding tissue. The lateral and axial spatial resolution capability of the scanner determines the ability of the scanner to provide a defined image of body structures in the lateral and axial dimensions of the scan slice. Other performance characteristics of scanners include the maximum depth into tissue of the scan slice at which visualization of structures in the patient can be obtained, the image gray level uniformity, and the accuracy of distance measurements between reflectors in the tissue that may be obtained from the scan slice that is displayed by the scanner. A particular scanner model may have superior performance in one of these characteristics compared to other scanners and lesser performance with respect to others. To some extent these performance criteria are not precisely quantifiable, but relate to the ability of human observers to obtain useful information from the displayed images. In addition, a particular scanner may change in its performance over time, due to loss of calibration or degradation of components, and such changes may affect some of the performance criteria more than others. It would thus be useful to have a standardized test of scanners which would allow rapid and convenient testing of all of these performance criteria of the scanner and reliable comparative testing of various models of scanners, and the ability to quantify the performance of scanners over time to detect any changes in performance.

SUMMARY OF THE INVENTION

The ultrasound phantom of the present invention is especially adapted to provide multiple testing capabilities for quality assurance on ultrasound scanners. The phantom allows testing of the performance of gray-scale ultrasound scanners with respect to several properties of the scanners. These include the ability to delineate the intersection of the plane of symmetry of the scan slice with the three- dimensional boundary of an object regardless of its shape, low contrast resolution of large objects, spatial resolution regarding lateral and axial dimensions, maximum visualization depth, image gray level uniformity, and distance measurement accuracy. Tests of a scanner utilizing the phantom of the invention may be repeated periodically, e.g., every six months. A scan configuration may be specified by the make and model of the scanner and scan head and by the scan parameters, including frequency, depth of image, focus, and so forth. Reproducible degradations found over time in the performance of the scanner in tests conducted on the phantom can be indicative of degradations in scanner or scan head performance and call for recalibration, repair, or replacement of the scanner or scan head.

The ultrasound imaging phantom for use in quality assurance testing of ultrasound scanners includes an ultrasound phantom container and a tissue mimicking background material contained within the phantom container. A first section in the tissue mimicking background material has an array of coplanar target spheres embedded in the background material, with each target sphere made of a tissue mimicking material having a selected contrast with the background material. Target spheres of various sizes may be utilized. The array of target spheres, which extends downwardly from a scanning window, allows testing of characteristics of the scanner such as the ability of the scanner to provide relatively sharp images of relatively small objects at various depths from the scan head and, equivalently, the ability of the scanner to delineate the boundary of an arbitrarily sized and shaped object. A second section in the background material has at least one target cylinder which has a contrast with the background material. Preferably there are a plurality of such target cylinders, with a set of target cylinders being of a large size relative to the target spheres, but having a relatively small contrast with the background material, e.g., 3 dB or less. Such large cylindrical targets allow testing of the ability of the scanner to detect large objects that have relatively low contrast. A third section has a planar array of elongated fibers embedded in background material. The fibers are located at known depths below the scanning window cover to which the ultrasound scanner is applied and give rise to strong echoes relative to the surround material comprising most of the section. The linear array of fibers allows lateral and axial resolution and the accuracy with which the scanner can measure distances between fibers to be determined. The phantom may also include a fourth section in the tissue mimicking background material which includes an array of small diameter target cylinders aligned in a plane and extending at increasing depths from the scanning window. The smaller diameter target cylinders have a higher contrast to the background material than the large diameter target cylinders, and provide a means for determining the maximum visualization depth of the scanner to be tested. Maximum depth of visualization can also be determined by measuring the maximum depth from which any detectable echoes return from the material in the section surrounding the small diameter cylinders.

The phantom container preferably has a planar ultrasound transmitting window cover, preferably wherein the plane of the array of spheres and the plane of the array of fibers are perpendicular to the ultrasound transmitting window cover. The elongated dimensions (i.e., along the axes) of the cylinders are also preferably parallel to the ultrasound transmitting window cover. The phantom may have two (or more) windows covered by preferably planar ultrasound transmitting window covers located at orthogonal positions, e.g., at the top of the phantom and at a side wall. One of the window covers may be perpendicular to the plane of the array of fibers and the other cover may be parallel to the plane of the array of fibers. The latter window may then be used to evaluate the accuracy of the scanner in measuring the distances between fibers in a direction perpendicular to the axial direction of the scan slice.

Elongated linear fibers may be embedded in the tissue mimicking background material in the plane of the array of spheres parallel to the ultrasound window and spaced from each other aid in alignment of the scan slice with the array of spheres and allowing the ability of the scanner to visualize the spheres as a function of depth to be gauged. Omnidirectional reflectors, e.g., formed as half knots in the fibers, may be located at regular intervals (e.g., 5 mm) to provide echoes for any direction of incidence of the ultrasound beam. Thus, echoes occur along the entire length of the fibers, even for sector scanners.

Visible lines and graphic markings may be provided on the outside surface of the ultrasound transmitting window cover to facilitate alignment of the scan head at the window with the various sections of the phantom and aid the user in understanding the configuration of target objects within the phantom that may be visualized on the image provided by the scanner.

The ultrasound quality assurance phantom of the present invention may thus be utilized to provide a rapid test of significant imaging performance characteristics of a scanner by taking scans of the various sections of the phantom and recording, and where appropriate, quantifying the results. Various scanner models may be tested using the same quality assurance phantom to provide reliable comparative tests of the scanners. In addition, a single scanner may be tested periodically to detect any changes in performance characteristics over time which would indicate the need for repair or recalibration of the scanner.

Further objects, features and advantages of the invention will be apparent from the following detailed description when taken in conjunction with the accompanying drawings.

DETAILED DESCRIPTION OF THE INVENTION

Figure 1:
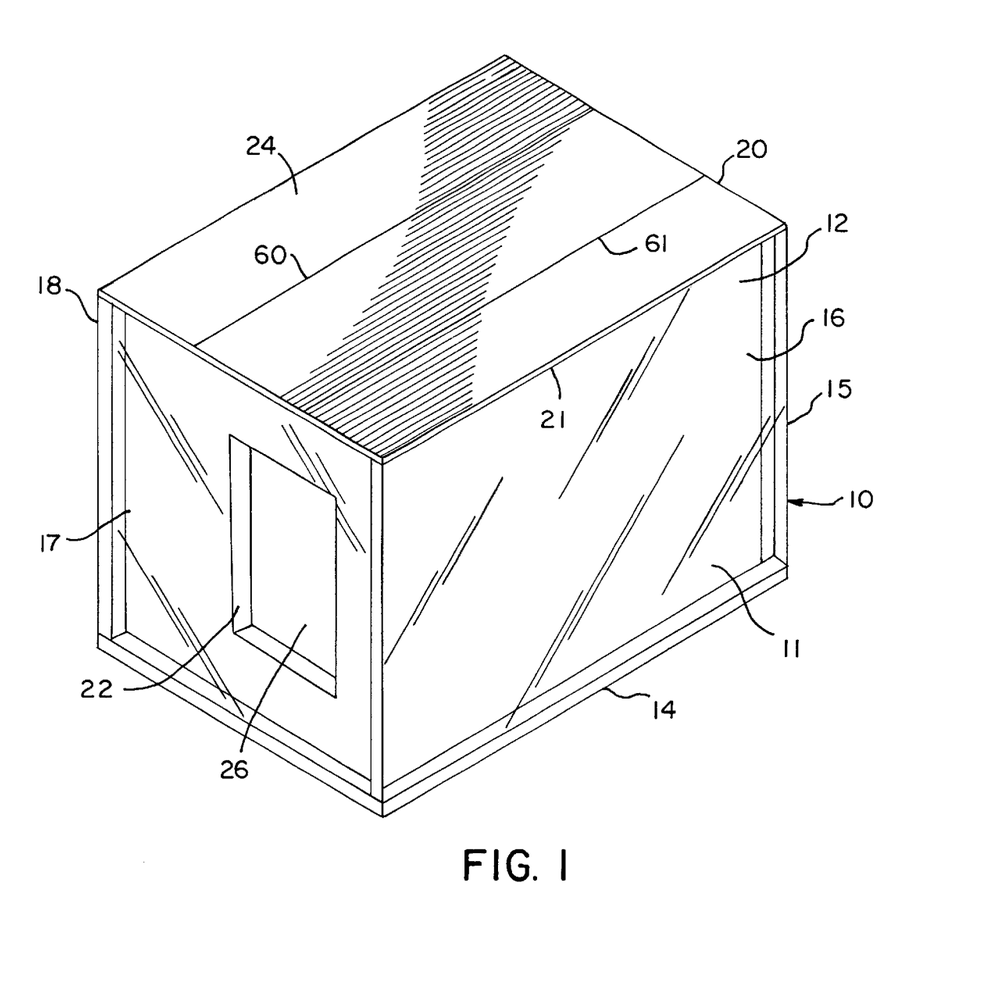
FIG. 1 is a perspective view of an exemplary ultrasound scanner phantom for quality assurance in accordance with the invention.

With reference to the drawings, an ultrasound scanner quality assurance phantom in accordance with the present invention is shown generally at 10 in FIG. 1. The ultrasound phantom 10 has a rigid container 11 for holding tissue mimicking material 12, comprised of a bottom wall 14 and side walls 15, 16, 17, and 18. The physical construction of the container 11 is not crucial, and any suitable materials that will hold the tissue mimicking material 12 within the container without substantial transmission of water vapor or air molecules therethrough may be utilized, such as acrylic plastic or ABS plastic. The container may be formed by adhering together plates of plastic, etc., or by one piece molding or any other convenient manufacturing process. The container 11 may also be formed in other configurations than the rectangular configuration illustrated in the figures, e.g., cylindrical, polygonal, etc.

For purposes of illustration, the container 11 of the phantom 10 includes a top window opening 20 defined by top margins 21 of the side walls 15–18, and a side window opening 22 formed in one of the side walls (side wall 17 for illustration). The top opening 20 is covered by a top window cover 24 which is sealed to the top window margins 21, e.g., with an epoxy glue. Similarly, the side scanning window opening 22 is covered with a side scanning window cover 26 which is sealed to the margins of the wall 17 around the opening 22, e.g., by being secured with epoxy adhesive to the inner side of the wall 17 at the borders of the side scanning window opening 22. The side window cover 26 could be secured to the exterior side of the wall 17, or to the parts of the wall 17 defining the opening 22, or in any other desired air and liquid tight manner.

The interior of the container 11 is filled with a water based tissue mimicking material 12 which is in a solid form, generally as a gel. The entire interior of the container 11, as sealed by the top window cover 24 and the side window cover 26, is filled with the tissue mimicking material 12 to form a tissue mimicking body which entirely occupies the space within the container and which may be in direct contact with the top scanning window cover 24 and the side scanning window cover 26. The filling of the container may be carried out as set forth in the aforesaid patents, e.g., as described in U.S. Pat. No. 5,625,137, by utilizing an additional filling opening (not shown) by which the tissue mimicking material in liquid form (e.g., prior to gelling for gel based tissue mimicking material) is introduced into the interior of the container. Any other method of filling the container may also be utilized.

A thin sheet of plastic may be used for the scanning window covers 24 and 26, e.g., films of polyurethane or saran plastics, which permit acceptable transmission of ultrasound through the window cover to the tissue mimicking material. The relatively high rate of transmission of water vapor through such plastic films would permit unacceptable desiccation of the water based tissue mimicking material within the container in an unduly short period of time, typically within a year or two or sometimes less. Consequently, when such types of plastic films are to be used, layers of oil based gels are preferably formed over the water based gels, with the oil based gels in contact with the window covers. A layer of oil based gel is neither needed nor desired by utilizing a cover which essentially blocks transmission of water vapor therethrough as well as blocking the transmission of air constituent molecules (e.g., oxygen, nitrogen, etc.) and organic molecules such as hydroxy typically found in the tissue mimicking material (e.g., n-propanol, ethylene glycol or glycerol). Thus, the top scanning window cover 24 and the side scanning window cover 26 are preferably comprised of a multi-layer film that is formed of at least a layer of metal on a layer of plastic and preferably between layers of plastic. The metal layer and plastic layer(s) are selected to be sufficiently strong and thick to provide structural integrity, but also to transmit ultrasound pulses from an ultrasound transducer therethrough without substantial attenuation or echoes. The metal foil layer provides blockage of vapor and air molecule transmission but is found not to significantly affect the transmission of the ultrasound pulses at the thicknesses required to block vapor and air transmission, while retaining the desired flexibility for the multi-layer film.

A preferred multi-layer film comprises a 100 micrometer total thickness multi-layer structure comprising a 0.00035 inch (8.89 micrometer) thick layer of aluminum foil between layers of plastic, a layer of low density polyethylene (⅔ mil/16.93 $\mu$m) on one side, and on the other side a layer of ScotchPak® heat sealable film from Minnesota Mining and Manufacturing Company (63 $\mu$m thick), with an additional layer of PET polyester (polyethylene terepthalate) (12.192 $\mu$m thick), preferably with white ink on the PET, adhered to the layer of low density polyethylene. This multi-layer film material is available commercially from American Packaging Company, Rochester, N.Y.

If desired, to protect the window covers 24 and 26 when the phantom is not in use, rigid displaceable guards (not shown) may be mounted to the container 11 and held in place over the window covers 24 and 26 until the phantom is to be used. The bottom wall 14 may also extend outwardly beyond the side walls 15–18 to provide a more stable base for the phantom. A handle (not shown) may be connected to the container for convenient carrying of the phantom.

The tissue mimicking material 12 includes background tissue mimicking material that may be formed in various conventional manners, as described in the foregoing patents. A preferred material set forth in U.S. Pat. No. 5,625,137 is a solid gel of an aqueous mixture of large organic water soluble molecules which, if desired, may contain an emulsion of fatty acid esters. Hydroxy compounds such as n-propanol may be incorporated in the mixture for controlling ultrasonic speed of propagation through the material. Preservatives, such as thimersol, may be added to the material mix as a preservative. Solid scattering particles, e.g., 45–53 micron diameter glass beads, may be added to the phantom body to increase the backscatter coefficient of the tissue mimicking material to a selected level. While such a material, which is described in further detail in the aforesaid U.S. Pat. No. 5,625,137, is preferred, the invention is not limited to this material, and any desired tissue mimicking material having appropriate backscatter coefficient and ultrasound propagation characteristics may be utilized.

Figure 2:
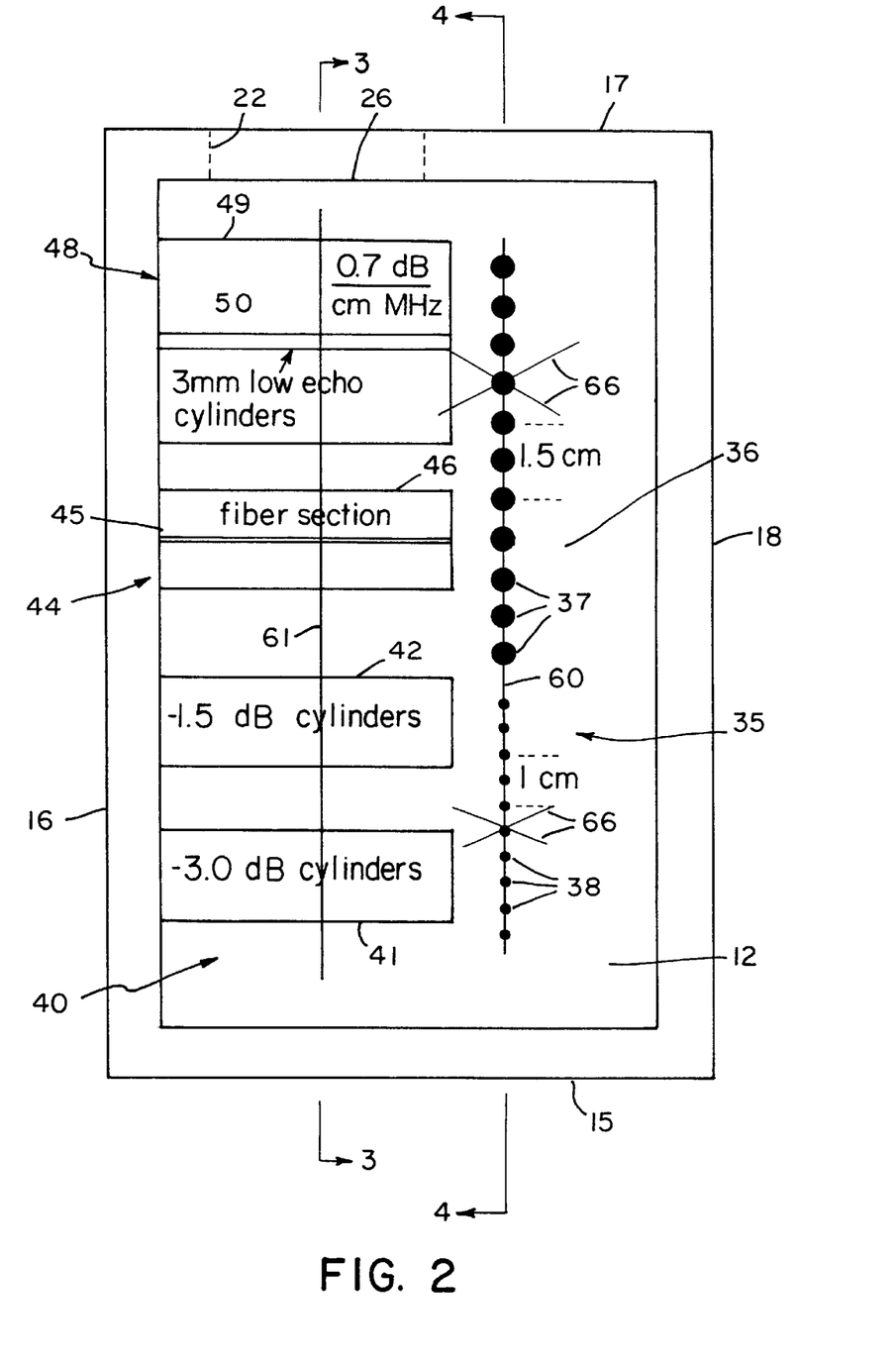
FIG. 2 is a top plan view of the phantom of FIG. 1 with the scanning window cover removed and illustrating the target objects within the various sections of the phantom.

The ultrasound phantom of the present invention includes several sections, each of which contains target objects embedded within the background material that are suited to test selected characteristics of ultrasound scanners and scan heads. With reference to FIG. 2, which shows a top view of the phantom with the ultrasound transmitting window removed, the distinct sections of the phantom include a first section 35 which includes a planar array 36 of spheres 37 and 38, a second section 40 which includes several target cylinders 41 of a first backscatter coefficient and target cylinders 42, of a second backscatter coefficient, a third section 44 containing a low echo background material 46 and an array of linear fibers 45 that lie in a plane, and a fourth section 48 containing a background material 49 of an attenuation coefficient that is much higher than the attenuation coefficient in other sections with which it is in contact and an array of small diameter cylinders 50 aligned in a plane within the background material 49.

Figure 3:
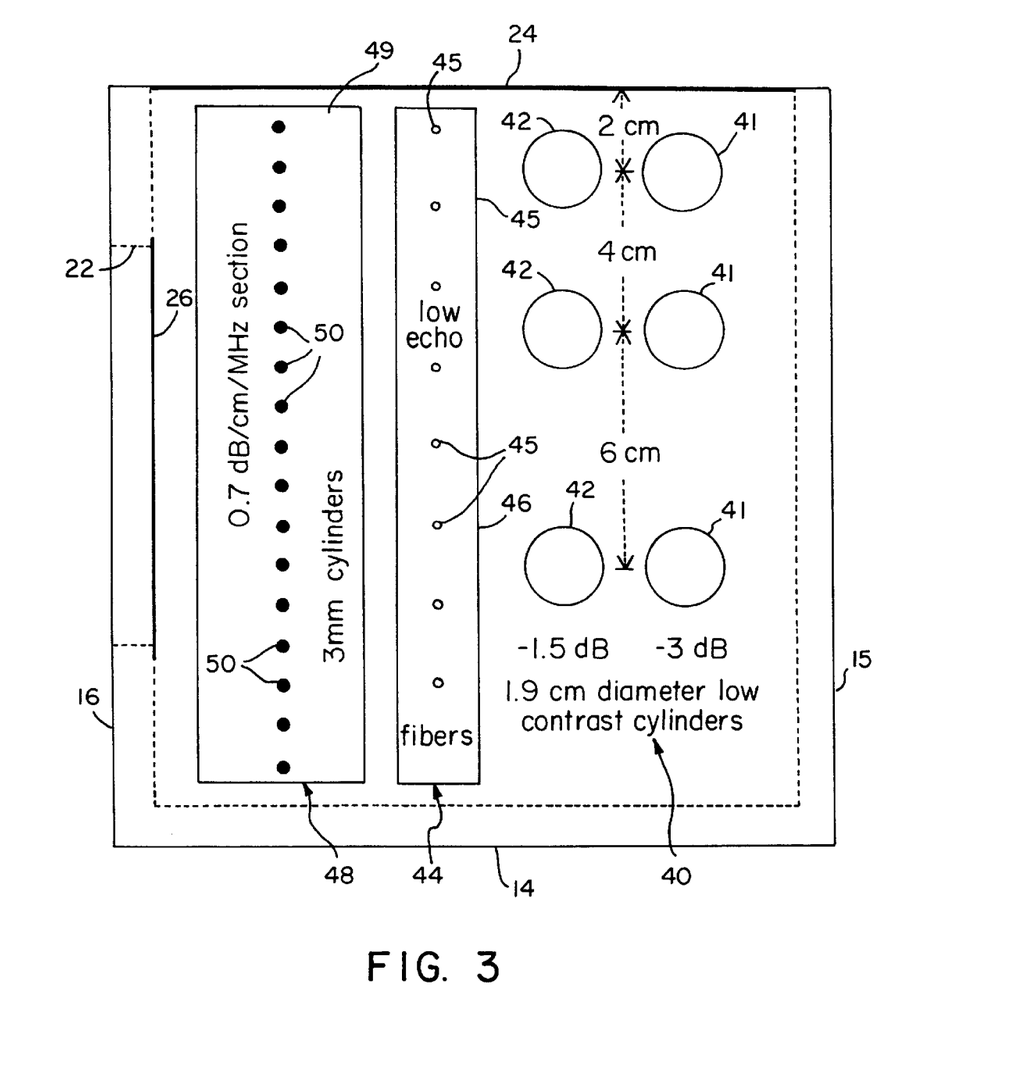
FIG. 3 is a cross-sectional view through the phantom taken generally along the lines 3—3 of FIG. 2.

With reference to the cross-sectional view of FIG. 3, taken through the middle of the sections 40, 44 and 48, the large diameter low contrast cylinders 41 and 42 in the section are preferably arranged in an array of a plurality of such target cylinders, with three of the cylinders 41 being illustratively shown in alignment at spaced depths beneath the scanning window cover 24 and three of the target cylinders 42 aligned at spaced depths beneath the scanning window cover 24 In the section 44, the linear fibers 45 are aligned in a planar array embedded within the low echo background material 46, with the fibers 45 aligned parallel to one another and lying in a plane that is perpendicular to the plane of the scanning window cover 24. The fibers 45 are arranged in the array in spaced relation at increasing depths beneath the scanning window cover 24. In the section 48, the elongated linear cylinders 50, of a much narrower diameter than the cylinders 41 and 42, are also aligned parallel to one another in spaced relation beneath the scanning window cover 24 and lie in a plane which is perpendicular to the plane of the scanning window cover 24.

Figure 4:
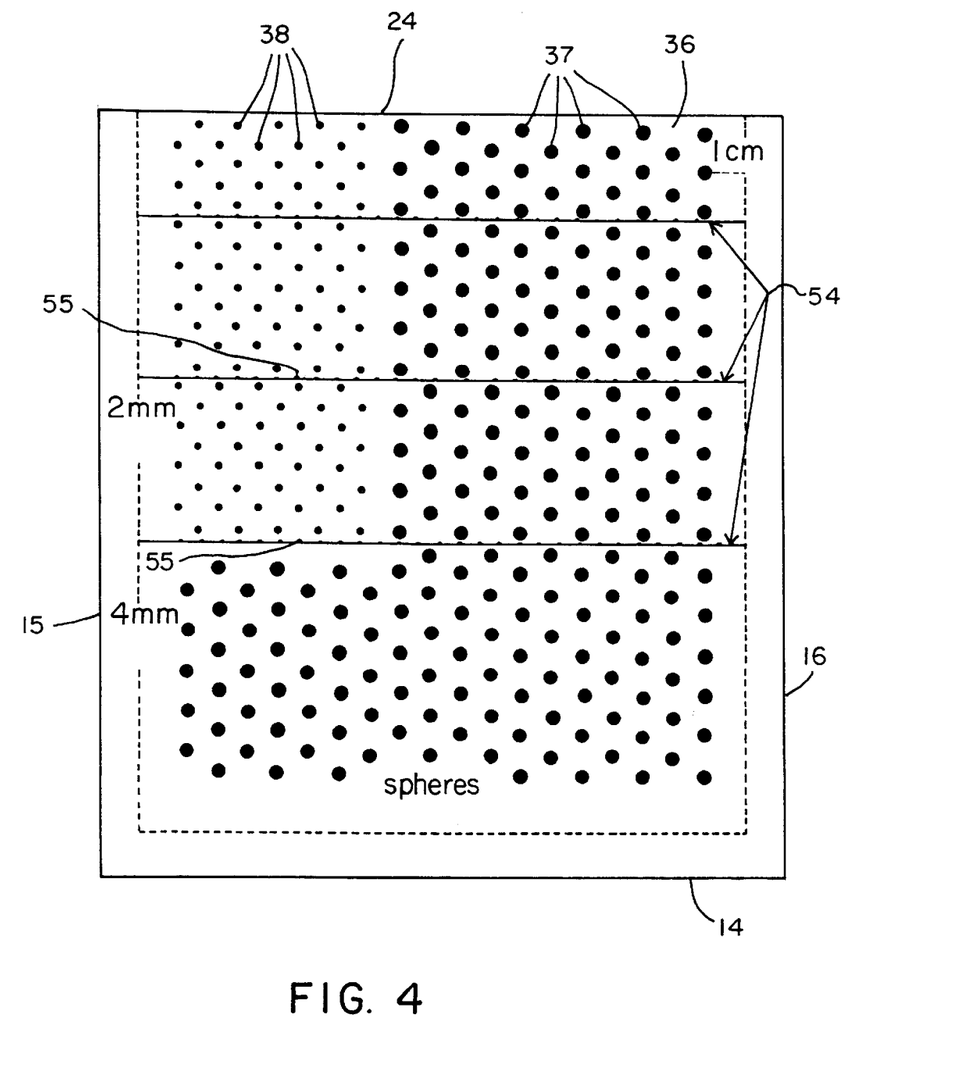
FIG. 4 is a cross-sectional view of the phantom taken generally along the lines 4—4 of FIG. 2.

A cross section taken through the plane of the array 36 of spheres is shown in FIG. 4. As illustrated therein, the array of spheres preferably includes a region of spheres 37 of a larger diameter arranged in a regular pattern lying in a plane that extends perpendicularly to the plane of the scanning window cover 24. Similarly, a region of smaller diameter spheres 38 is formed in a regular array in the same plane as the plane of the spheres 37, again perpendicular to the scanning window cover 24. The spheres 37 and 38 are located with their centers coplanar. One or more elongated linear fibers 54 are preferably located in the plane of the array 36 at spaced depths beneath the scanning window cover 24 and aligned parallel to one another and parallel to the plane of the scanning window cover. The fibers 54 are located at known depths beneath the scanning window cover 24 and aid in alignment of the scan slice with the array of spheres. Preferably, the fibers 54 have omnidirectional reflectors 55 formed therein at selected positions along the length of the fibers. The omnidirectional reflectors may be formed as knots in the fibers.

A preferred and suitable ultrasonic propagation speed for the entire tissue mimicking material 12 within the container is 1540 m/s±5 m/s. A preferred and suitable attenuation coefficient is 0.50±0.05 dB/cm/MHz (from 1 through 10 MHz) throughout the mass of the tissue mimicking material 12 except in the section 48 which is utilized for depth of visualization tests, where a preferred attenuation coefficient is 0.7±0.5 dB/cm/MHz. At the interfaces of the background tissue mimicking material with the spheres 37 and 38 and the cylinders 41, 42 and 50, the acoustic impedances are preferably matched to within 0.15%. Except in the regions of the spheres 37 and 38, the cylinders 41, 42 and 50, and the material 46 in the section 44, the backscatter coefficient throughout the background tissue mimicking material in all sections is preferably $3.7 \times 10^{-6}$ (±3 dB) cm$^{-1}$ sr$^{-1}$ MHz$^{-4}$ f$^4$, where f is the ultrasonic frequency between 1 and 10 MHz. This backscatter coefficient conforms to the recommended value for phantoms given in Appendix B of Standard Methods for Measuring Performance of Pulse Echo Ultrasound Imaging Equipment, American Institute of Ultrasound in Medicine, 1990.

Preferred sizes for the spheres 37 and 38 are 4 mm and 2 mm, respectively, and a preferred backscatter coefficient of the tissue mimicking material forming the spheres 37 and 38 with respect to the background tissue mimicking material is −35 dB. In the large low-contrast cylinders 41, the backscatter coefficient relative to the background tissue mimicking material is preferably −3.0 dB, and in the low contrast cylinders 42 the backscatter coefficient relative to the background material is preferably −1.5 dB. The backscatter coefficient of the material 46 in the section 44 containing the fibers 45 is preferably about −28 dB relative to the background tissue mimicking material, and the attenuation coefficient in this section is preferably 0.50±0.05 dB/cm/MHz.

The backscatter coefficient relative to the background in the narrow diameter elongated cylinders 50 may also be −35 dB. The fibers 45 may be formed of nylon (e.g., 0.1 mm diameter). Exemplary dimensions for the spheres 37 in the array 36 are 4 mm diameter with centers spaced 1.5 cm in the horizontal direction and 1 cm in the vertical direction, and for the spheres 38, exemplary dimensions are 2 mm diameter with a horizontal and vertical spacing between centers of the spheres of 1 cm. Exemplary dimensions for the large low contrast cylinders 41 and 42 are 1.9 cm diameter, with the spacing of the cylinders 41 and 42 beneath the window cover 24 to the central axis of the cylinders being at depths of 2 cm, 6 cm and 12 cm beneath the plane of the window cover 24. Exemplary dimensions for the narrow diameter elongated cylinders 50 are 3 mm diameter and about 5.5 cm in length. The fibers 45 and the cylinders 41 and 42 may also have exemplary lengths of about 5.5 cm.

The material of the target spheres 37 and 38, the cylinders 41 and 42, and the cylinders 50 may be formed as described in the foregoing patents, particularly U.S. Pat. No. 5,625,137, incorporated by reference, and discussed, for example, in E. L. Madsen, G. R. Frank and F. Dong, "Liquid or Solid Ultrasonically Tissue-Mimicking Materials with Very Low Scatter," Ultrasound in Med. & Biol., Vol. 24, No. 4, 1998, pp. 535–542. However, it is understood the ultrasound phantom of the present invention is not limited to these specific tissue mimicking materials.

The following is an example of suitable compositions by weight percent of the base gel material (suspended glass bead scatters or powdered graphite may be incorporated in the base gel as described below): n-propanol: 1.96; distilled, deionized water: 28.98; condensed milk (concentrated by reverse osmosis, filtered through an 8 micrometer opening filter, and containing 2 grams per liter of a preservative such as thimerosal): 67.49; agarose (catalog # A-4679, Sigma Chemical Company, St. Louis, Mo.): 1.57. Each component of the phantom may have the concentrations of #3000E glass beads (Potters Industries, Inc., Valley Forge, Pa.) and/or of #9039 graphite powder given in Table 1 below (Superior Graphite Company, Chicago, Ill.). The Potters beads have a mean diameter of about 20 micrometers. Values represent the number of grams of the particles per liter of gel.

TABLE 1

| Material | Glass Beads | Graphite |
| --- | --- | --- |
| Background SURROUNDING spherical lesions, low contrast cylinders, higher attenuation section and fiber section | 6 | 0 |
| Higher attenuation section surrounding the 3 mm diameter cylinders | 6 | 20 |
| 3 mm diameter cylinders in the higher attenuation section | 0 | 26 |
| 2 mm and 4 mm diameter spheres AND the fiber section | 0 | 0 |
| −3.0 dB low contrast cylinders | 3 | 0 |
| −1.5 dB low contrast cylinders | 1.5 | 0 |

To aid in the placement of the ultrasound scanning head over the target objects located in the various sections of the phantom, alignment lines 60 and 61 are preferably permanently marked on the outer surface of the window cover 24, as illustrated in FIG. 1. These alignment lines 60 and 61 are also shown for purposes of illustration in FIG. 2 to illustrate the position of the line 60 in alignment with the plane of the array of spheres 36 and of the line 61 extending perpendicular to the elongated direction of the cylinders 41 and 42, the fibers 45, and the narrow diameter cylinders 50, and approximately extending through the centers thereof. To aid in the use of the phantom, it is preferred that graphic information illustrating the positions of the target objects substantially identical in appearance to that shown in FIG. 2 be imprinted on the outer surface of the window cover 24. These graphic markings on the cover surface are positioned directly over the corresponding target objects in the tissue mimicking material below, aiding the user in aligning the scan head with the desired target objects. Preferably, graphic markings substantially as shown in FIG. 3 are printed on a side wall of the container (e.g., the side wall 16), and a graphic pattern substantially as shown in FIG. 4 is also preferably printed on the other side wall 18 of the phantom container to aid the user in identify the target objects to be imaged by the ultrasound scanner.

As also illustrated in FIG. 2, if desired, alignment fibers 66 may be embedded in the background tissue mimicking material positioned to cross over at an intersection point which lies in the plane of the array of spheres 36, with the fibers 66 aligned in a plane that is parallel to the plane of the scanning window cover 24 at a position slightly below the window cover (e.g., at 2 mm depth). These crossed fibers may be utilized for precisely locating the center of the plane of the spheres 36 at the 2 mm depth, and graphic markings may be formed, to identify the position of the fibers 36, on the outer surface of the window cover 24.

Figure 5:
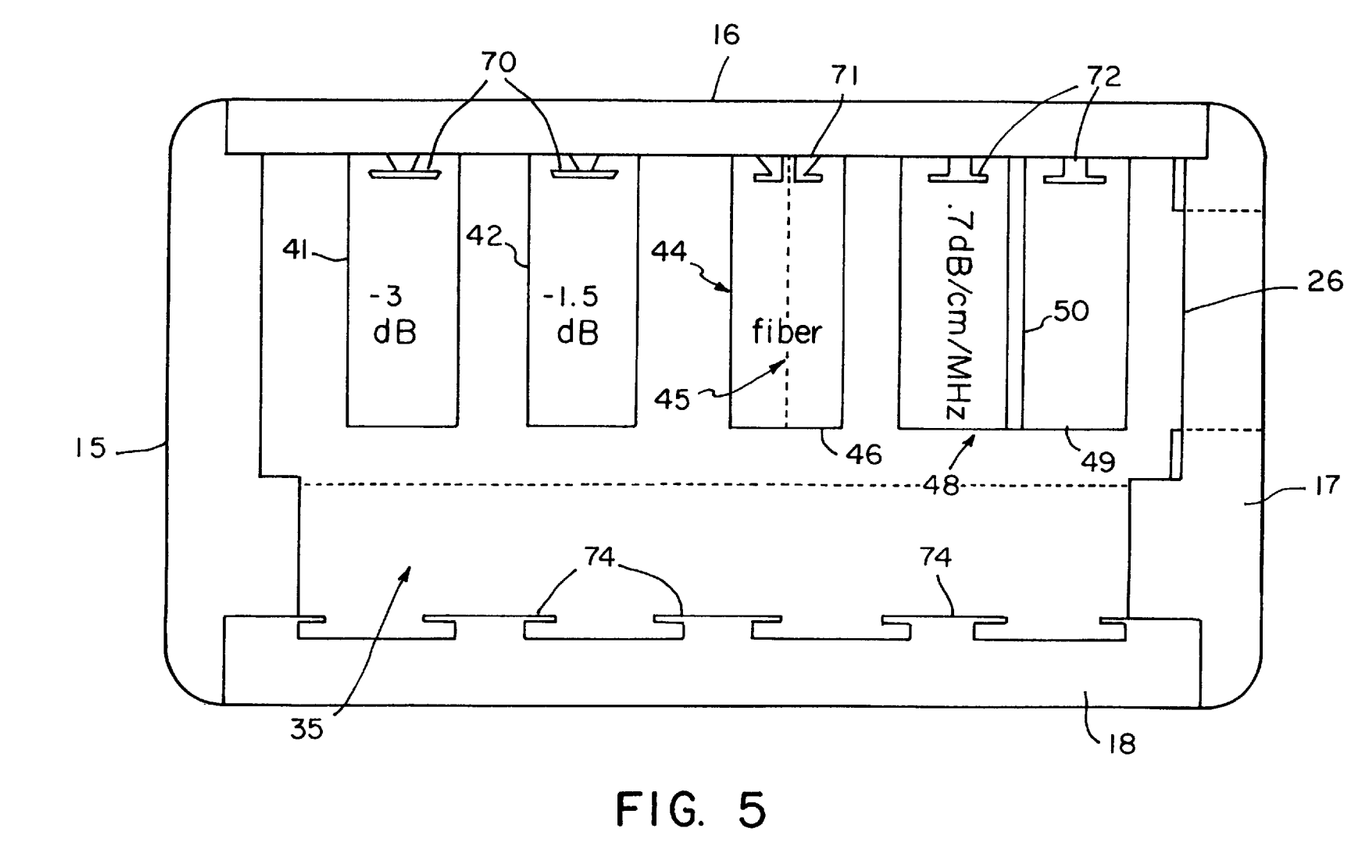
FIG. 5 is a plan view of a phantom container with anchoring structures for the tissue mimicking material.

The sections 44 and 48 which have background material which differs from the background material for the other sections are preferably pre-made in molds prior to introduction into the container 11 of the phantom. As shown in FIG. 5, the large diameter cylinders 41 and 42 are preferably formed to be secured to "toadstool" shaped anchors 70 on the side wall 16, and the sections 44 and 48 are preferably formed to be secured to elongated anchors 71 and 72, respectively, which project from the side wall 16. Anchoring structures 74 may also project from the side wall 18 in the section 35, to engage the background material in that section. The anchors 70, 71, 72 and 74 are preferably shaped to minimize return of unwanted echoes to the scan head. In one manner of producing the section 48 with the small diameter cylinders, a mold can be prepared containing a base plate with the anchor structures 72, which is then filled with liquid tissue mimicking material gel, with stainless steel rods inserted in the mold at the positions of the cylinders 50. After the gel is solidified, the rods are withdrawn and the holes filled with a low echo tissue mimicking material appropriate for the cylinders 50. The mold is then removed and the gel cylinders 50 clipped to the proper length. The base plate may then be glued into a socket in the side wall 16 of the phantom container. The section 44 container the fibers 45 may be formed in an equivalent manner, with the fibers positioned in the mold instead of the rods for the cylinders and with the fibers anchored (e.g., with glue) in the base plate. After the section is formed, the mold is removed and the fibers 45 clipped to their proper length, and the base plate is then glued into a socket in the side wall 16 of the phantom container.

The ultrasound phantom of the present invention is suited to allow several performance characteristics of ultrasound scanners to be tested quickly and conveniently. Each of the sections 35, 40, 44 and 48 of the phantom allows different performance characteristics of the scanner to be evaluated by the user based on the image of the target objects in these sections that is presented to the user by the scanner. Suggested procedures for the use of the phantom for evaluating the performance of a scanner are discussed below.

A first test is carried out by detecting all possible spheres in the array of spheres in the section 35, which is facilitated by positioning the scan head on and along the line 60 marked on the outer surface of the window cover 24. The purpose of the test is to determine the depth range over which small spheres can be detected in the background speckle pattern. The smaller the sphere that can be detected, the better the scanner will delineate during medical examination the boundary of an object such as a spiculated tumor or a blood vessel that is not perpendicular to the scan slice. Ideally, an imager would have a very thin scan slice and would show the variations in the boundaries of a spiculated tumor as the scanning head is moved to different positions above the tumor. The two regions of spheres 37 and 38 in the array of spheres 36 are coplanar and provide very low echo (−35 dB) spheres. The plane of symmetry of the scan slice (the "center" of the scan slice) must be superimposed on the plane containing the centers of the spheres so that the detectability of the spheres is optimized. The phantom may provide two aids for centering the scan slice on the spheres. One aid is the nylon fibers 54 (e.g., 3 nylon fibers, 0.1 mm diameter) that are embedded in the plane containing the sphere centers. These are preferably at depths of 2.75, 6.75 and 10.75 cm and have omnidirectional reflectors 55 at approximately 5 mm intervals along their lengths. The two pairs of crossed nylon fibers 66 (each pair touching and crossing at an angle of, e.g., 60°) are portioned with the crossing points of the fibers lying in the plane containing the sphere centers. The fibers may be at a shallow depth, e.g., 2 mm from the scanning window cover, to allow alignment of the scan slice with the sphere plane at a position very near the scanning window.

In carrying out a test, the scan parameters desired are selected, including depth of image, focus depth and power level. These parameters should be displayed on the scanner monitor for recording on hard or soft copy. The scan head is positioned parallel to the plane containing spheres, but displaced about 1 cm toward the nearest wall of the phantom, and the overall gain and TGC controls are adjusted until the image looks uniform and has a mean gray level typical of that used clinically. The information regarding these parameters displayed on the monitor should be checked or recorded in a notebook and the background reference image should be recorded digitally or on hard copy. The scan head is then positioned so that the scan slice is approximately superimposed on the spheres and one of the two fiber 66 crossing points is near the center of the scan head face. The scan head is then centered over the proximal spheres. If the scan head is a linear array or curved linear array, it is usually possible to see two distinct echoes from each of the crossed fibers 66 by movement of the scan head perpendicularly to the scan slice. The scan head is centered over the proximal spheres when the two fiber images blend together to form an echo of minimum lateral extent. If the crossed fibers are not visible, the scan head may be aligned by inspection so that the scan slice is centered on the line 60 marked on the scanning window cover. By rotating the scan head without moving the center of the scan head face, the alignment of the scan slice with the spheres is completed using echoes from whichever of the fibers 54 lie in the depth range of the image. If a linear array is being tested, each of the fibers 54 should appear as a uniform echo along its length with small darkened interruptions at the omnidirectional reflectors 55. If a curved linear array or a phased array is being tested, echoes from the omnidirectional reflectors on the fiber should provide brightly visible marks on the image from these reflectors as well as from that part of each fiber which is nearly perpendicular to the beam direction. Once alignment of the scan slice has been accomplished, the image may be frozen and labeled on the monitor, and stored for the particular sphere size 37 or 38. The test should be repeated for each of the two sphere sizes.

The images may be examined and estimates may be made of the limits of the depth range (resolution zone) over which spheres of each size can be detected to specify the minimum depth and the maximum depth of the resolution zone. Random fluctuations in speckle pattern can look like detected spheres, and to avoid these false positives and determining resolution zone limits, the background image (which contain sample false positives), can be referenced along side the images where the spheres are present.

Testing of the ability of the scanner to resolve images of objects having low contrast with the surrounding material may be carried out using the section 40 containing the large cylinders 41 and 42. The two sets of cylinders 41 and 42 preferably differ in contrast, e.g., with the cylinders 41 having a −3 dB contrast and the cylinders 42 having a −1.5 dB contrast. The axes of all of these cylinders are preferably parallel to one another and to the scanning window covers, and therefore the cylinders may be appropriately imaged with the scan slice perpendicular to their axes. When the scan slice is perpendicular to the axes of the cylinders, there will be small specular echoes at the proximal and distal surfaces of each cylinder. These echoes can be used to identify the cylinder positions, but the user may avoid the specular echoes by tilting the scan slice somewhat. In making the test, the scan parameters desired are selected, including depth of image, focus depth and power level. As before, these parameters should be displayed on the monitor for recording. The scan slice is positioned perpendicular to the axes of the cylinders and central to the lengths of the cylinders, and the overall gain and TGC controls are adjusted until the image of the background surrounding the cylinders looks uniform and has mean gray level typical of that used clinically. The information on the parameters displayed on the monitor should be checked and recorded. An image is then obtained and frozen of the low contrast cylinders 41 and 42 and the user may then note which of the various cylinders 41 and 42 at varying depths have been resolved based upon contrast, and the image should be then recorded digitally or in hard copy.

The section 44 containing the fibers 45 may be utilized for lateral and axial resolution tests. There are situations where knowledge of the lateral and/or axial resolution of the scanner will have greater importance than the elevational (slice width) resolution. Such situations usually involve alignment of surfaces or cylinders perpendicular to the scan slice. An example occurs when the scan slice is aligned perpendicular to a blood vessel and it is desired to determine the wall thickness or to image the entire circular wall. The better the lateral and axial resolution, the more accurate the depiction of the vessel wall. With the propagation axis perpendicular to the wall, accuracy of wall thickness measurements is enhanced by better axial resolution related to specular reflections at the wall boundary.

The section 44 contains a plurality of elongated fibers 45 (e.g., 0.1 mm diameter parallel fibers at depths of 1, 3, 5, 7, 9, 11, 13 and 15 cm from the scanning window cover). The fibers are embedded in a very low echo background material 46 so that background echoes do not interfere with the measurements. In this section, the propagation speed is 1540 m/s and the attenuation is 0.5 dB/cm/MHz.

Axial resolution is assessed by determining the axial extent of one of the fiber images. Any of the fibers 45 can be addressed since axial resolution is not a significant function of depth. In carrying out the tests, the scan head is positioned on the line 61 marked on the outside surface of the scanning window cover above the section 44 so that the scan slice is approximately perpendicular to the fibers 45. A fiber is chosen at a convenient depth, the overall gain is set at least 20 dB below the maximum, and the TGC is adjusted until the fiber is barely detectable even though its echo has been maximized by appropriate wobbling (angling) of the scan slice. The image is then frozen and the axial extent of the fiber image is then measured with electronic calipers. Some estimation or interpretation may be necessary because the axial extent will usually be less than 1 mm. Information should be recorded to indicate that the fiber at the chosen depth is barely detectable, and the image is recorded digitally or in hard copy. The image may then be unfrozen and the overall gain may be increased by, e.g., 6 dB. The scan slice may be wobbled until the image of the same fiber is again maximized. The image is then frozen and the procedure above is performed, but noting that the axial width corresponds to 6 dB above the barely detectable fiber.

Lateral resolution will generally be depth dependent. Thus, measurement should be done at all available fiber depths. There are two common situations, one where the TGC can be varied independently for small depth increments, usually using a set of about eight TGC sliders on the scanner console, and the other in which there is only one control for TGC.

Where the TGC can be varied independently for small depth increments, a suggested procedure begins by setting the overall gain at least 20 dB below the maximum. The scan slice is then aligned along the line 61 on the scanning window cover, which is nearly perpendicular to the fibers so that the scan slice is nearly perpendicular to the fibers. The scan slice may then be wobbled until echoes from the fibers are maximized and, maintaining echo maximization, the TGC may be reduced at each imaged fiber until it is barely visible. The image is then frozen and using the electronic calipers the lateral extent in mm of the echo for each fiber is determined. Information should then be recorded that the fibers are barely detectable and the lateral extent of each fiber image next to its image should be recorded. The image should be recorded digitally or on hard copy. The image is then unfrozen and, without changing the TGC settings, the overall gain is then increased, e.g., by 6 dB. The echoes are then maxinized by wobbling the scan slice and freezing the image, and then the procedure above is repeated except that the image fibers are noted as being 6 dB above barely detectable. These steps may be repeated with the overall gain increased by, e.g., 20 dB instead of 6 dB. Evidence of side lobes and clutter may be observed. The very low scatter background material makes such detailed inspection of the pulse-echo response possible.

Where the TGC cannot be varied independently for small depth increments, a procedure may begin by setting the overall gain at least 20 dB below the maximum. The scan slice is then centered along the line 61 so that the scan slice is nearly perpendicular to the fibers. The scan slice is then wobbled until echoes from the fibers are maximized and, maintaining echo maximization, the TGC is reduced until the fiber 45 at 1 cm depth is barely visible. The image is then frozen, and using the electronic calipers the lateral extent and mm of the echo is then determined. This information is entered on the monitor that the fiber at 1 cm depth is barely detectable and the lateral extent of the fiber image next to its image is recorded. The entire image is recorded digitally or on hard copy. The image is then unfrozen and, without changing the TGC settings, the overall gain is increased by, e.g., 6 dB. The echo is maximized by wobbling the scan slice and freezing the image. The procedure above is repeated except it is noted that the image fibers are 6 dB above barely detectable. These steps are repeated for each of the remaining fibers replacing 1 cm with 3 cm, 5 cm, etc. The foregoing steps may also be repeated for fibers at one or more depths with the overall gain increased by 20 dB instead of 6 dB to search for evidence of side lobes and clutter.

Maximum depth of visualization tests may be carried out using the section 48. There will be a maximum depth of visualization (MVD) from which useful echoes from tissues will be detectable. Generally, the lower the frequency, the greater the MVD. The section 48, which may be 4 cm wide, has an attenuation coefficient in the entire section of 0.7 dB/cm/MHz. This higher attenuation than in the other sections facilitates determination of MVD for low frequency scan heads without making the phantom inconveniently deep.

There are various methods for assessing MVD and the suggested procedure for determining each is given below.

In a first procedure based on deepest random speckle echoes, the scan head is centered over the section 48 with the scan slice perpendicular to the narrow diameter cylinders 50 and aligned with the line 61 on the scanning window cover. The overall gain and/or TGC is raised until the randomly positioned speckle echoes arising from within the section occur to a maximum depth. The maximum depth in cm of stationary random speckle echoes is estimated and recorded.

Specular reflections may be visible in the image from the proximal and distal surfaces of the, e.g., 3 mm diameter cylinders 50, which simulate blood vessels. These cylinders are centered at, e.g., 1, 2, 3, 4, 5, 6, 7, 8, 9, 10, 11, 12, 13, 14, 15, 16 and 17 cm depth. In carrying out this procedure, the scan head is centered over the section 48 with the scan slice perpendicular to the cylinders 50. The scan head is then wobbled to maximize echoes from the cylinders 50. The overall gain and/or TGC is increased to visualize the deepest echoes from the cylinder surfaces which are stationary when the scan head is stationary. The image is then frozen and the deepest cylinder 50 from which echoes are detectable is recorded. This value is the MVD.

The MVD may be determined in the absence of specular echoes by repeating the first steps of the procedure above and slowly angling the scan slice away from the nearest phantom wall until specular echoes have just disappeared. The material composing the cylinders 50 has a much lower backscatter (echogenicity) than that of the surroundings. The image is then frozen and an estimate is made of the deepest detectable cylinder 50 based on its low echo characteristics. This form of the MVD is then recorded.

The phantom 10 may also be utilized to determine image uniformity. Ideally, if the tissue being scanned has uniform ultrasonic properties, the entire image should demonstrate a uniform average gray level. This may be done with the phantom 10 by positioning the scanning head for a scan slice located about 1 cm from the line 60 designating the position of the plane of the spheres 36, on the side of the line 60 away from the sections 40, 44 and 48. The scan slice is then wobbled to obtain the most uniform image and then uniformity is maximized by adjusting the overall gain and TGC. A deficiency of some scanners is that the lateral edges of the image are darker (lower echo) than the central region. Also, there are sometimes unavoidable axial variations in echo level. The image is then frozen and labeled as a "uniformity check" and is recorded in digital or hard copy. It should be noted whether there are abrupt depth-dependent variations in image brightness such as might be associated with the use of multiple transmit focal zones. The image may be evaluated to determine whether there are side-to-side variations in brightness. Narrow shadows should be looked for starting at zero depth such as would occur when there is "element drop-out."

To determine vertical or axial distance measurement accuracy, the scan head may be placed on the line 61 of FIG. 2 over the fibers 45 in the section 44 and the overall gain and TGC settings reduced until the fiber echoes are minimal with scan slice wobble maximizing echoes. The image is then frozen and, using the electronic calipers, distances between pairs of fibers at depths of 1, 3, 5, 7, 9 and 11 cm are then measured. The measured distances are compared with known distances between the fibers.

For lateral distance measurement accuracy, the scan head may be placed on the side window cover 26 (see FIG. 1) with the scan slice perpendicular to the fibers in the section 44. The scan slice is wobbled to maximize fiber echoes while the TGC and/or overall gain is adjusted to obtain barely visible echoes from the fibers. The image is then frozen and, using the electronic calipers, distances between pairs of fibers at depths of 1, 3, 5, 7, 9 and 11 cm are then measured. The measured distances are then compared with the known distances between the fibers.

It is understood that the invention is not confined to the particular embodiments set forth herein as illustrative, but embraces such modified forms thereof as come within the scope of the following claims.

What is claimed is:

1. An ultrasound imaging phantom for use in quality assurance testing of ultrasound scanners, comprising:
   (a) an ultrasound phantom container;
   (b) a tissue mimicking background material contained within the phantom container;
   (c) a first section in the tissue mimicking background material having an array of coplanar target spheres embedded in the background material, wherein each target sphere is made of a tissue mimicking material, a second section in the background material having at least one target cylinder embedded in the background material, and a third section having a planar array of elongated fibers embedded in the background material, wherein the tissue mimicking material of the target spheres and target cylinders differs from the background material in which they are embedded by at least one of ultrasonic speed, backscatter coefficient or attenuation coefficient.

2. The phantom of claim 1 wherein the array of spheres includes a first region of the array containing spheres of a first size and the second region of the array containing spheres of a second size.

3. The phantom of claim 1 wherein the phantom container has a planar ultrasound transmitting window cover, and wherein the plane of the array of spheres and the plane of the array of fibers are perpendicular to the ultrasound transmitting window cover.

4. The imaging phantom of claim 3 including at least one elongated linear fiber lying in the plane of the array of spheres and parallel to the ultrasound window.

5. The phantom of claim 4 wherein there are at least two elongated linear fibers embedded in the tissue mimicking background material in the plane of the array of spheres parallel to the ultrasound window and spaced from each other.

6. The phantom of claim 4 wherein the fiber has at least one omnidirectional reflector formed thereon.

7. The phantom of claim 6 wherein the omnidirectional reflector comprises a knot formed in the fiber.

8. The phantom of claim 1 wherein the section containing a target cylinder includes a plurality of target cylinders of a first diameter, and including a fourth section having a plurality of target cylinders of a second diameter smaller than the first diameter embedded in the background material.

9. The phantom of claim 8 wherein the phantom container includes a planar ultrasound transmitting window cover, wherein the plane of the array of spheres is perpendicular to the ultrasound transmitting window and wherein the sections containing the larger diameter cylinders, the smaller diameter cylinders, and the fibers are generally in alignment with each other, and with the elongated dimensions of the cylinders and the fibers perpendicular to the plane of the array of spheres and parallel to the ultrasound transmitting window cover.

10. The phantom of claim 9 further including a visible line marked on the outer surface of the ultrasound transmitting window at a position lying in the plane defined by the array of spheres and a second line marked on the outer surface of the ultrasound transmitting window parallel to the first line and generally centered over the sections containing the large diameter cylinders, the small diameter cylinders and the elongated fibers.

11. The phantom of claim 9 wherein there are two sets of large diameter cylinders with the cylinders in one set having a different backscatter coefficient than the cylinders in the other set and both of which differ from the backscatter coefficient of the background material.

12. The phantom of claim 11 wherein the backscatter coefficient of the large diameter cylinders is selected so that the contrast between the large diameter cylinders and the background material is about 3 dB or less.

13. The phantom of claim 9 wherein in the section containing the array of fibers has a backscatter coefficient much lower than that of the tissue-mimicking material in the other sections.

14. The phantom of claim 1 wherein the backscatter coefficient of the spheres in the array of spheres relative to the background material is −35 dB or less, the backscatter coefficient of the target cylinders relative to the background material is −3.0 dB or less, and the backscatter coefficient of the section containing the array of fibers is −28 dB or less.

15. The phantom of claim 1 further including at least one pair of crossed elongated fibers embedded in the background material, the crossed fibers intersecting and engaging one another at a point that lies in the plane of the array of spheres and with the crossed fibers lying in a plane perpendicular to the plane of the array of spheres.

16. The phantom of claim 1 wherein the background tissue mimicking material comprises an aqueous mixture of large organic water soluble molecules and a gel forming material.

17. The phantom of claim 16 wherein the background material includes a hydroxy compound and a preservative.

18. The phantom of claim 16 wherein the background material additionally includes solid scattering particles.

19. The phantom of claim 16 wherein the spheres in the array of spheres and the cylinders are formed of the background material but differing from the background material in components such that at least one of the ultrasonic speed, attenuation coefficient or backscatter coefficient differs from that of the background material.

20. The phantom of claim 1 wherein the phantom container includes a top planar ultrasound transmitting window cover wherein the plane of the array of fibers is perpendicular to the ultrasound transmitting window and wherein the phantom container includes a side planar ultrasound transmitting window over the plane of which is perpendicular to the plane of the top window cover and parallel to the plane of the array of fibers.

21. The phantom of claim 20 wherein the section containing the array of fibers has a backscatter coefficient much lower than that of the tissue mimicking material in other sections of the phantom.

22. An ultrasound imaging phantom for use in quality assurance testing of ultrasound scanners, comprising:
  (a) an ultrasound phantom container;
  (b) a tissue mimicking background material contained within the phantom container;
  (c) a plurality of sections in the tissue mimicking background material, one of the sections having a planar array of elongated target cylinders embedded in the background material, wherein the material of the target cylinders differs from the background material in which they are embedded by at least one of ultrasonic speed, background coefficient or attenuation coefficient, and wherein the background material in the section in which the target cylinders are embedded is in contact with the background material in at least one other section and has a higher attenuation coefficient than the background material of the section it is in contact with.

23. The phantom of claim 22 wherein the phantom container has an ultrasound transmitting window cover, and wherein the plane of the array of cylinders is perpendicular to the ultrasound transmitting window cover.

24. The phantom of claim 22 wherein the attenuation coefficient of the background material in which the cylinders are embedded is at least 0.7 dB/cm/MHz and the attenuation coefficient in the background material in the section in contact therewith is 0.5 dB/cm/MHz or less.

25. An ultrasound imaging phantom for use in quality assurance testing of ultrasound scanners, comprising:
  (a) an ultrasound phantom container;
  (b) a tissue mimicking background material contained within the phantom container;
  (c) a first section in the tissue mimicking background material having an array of coplanar target spheres embedded in the background material, wherein each target sphere is made of a tissue mimicking material, a second section in the background material having at least one large diameter target cylinder embedded in the background material made of tissue mimicking material, a third section having a planar array of elongated fibers embedded in the background material, and a fourth section having a planar array of a plurality of elongated small diameter target cylinders of tissue mimicking material embedded in the background material, wherein the tissue mimicking material of the target spheres and of the large diameter and small diameter target cylinders differs from the background material in which they are embedded by at least one of ultrasonic speed, backscatter coefficient or attenuation coefficient; and
  (d) a planar ultrasound transmitting window cover, and wherein the plane of the array of spheres, the plane of the array of fibers and the plane of the array of target cylinders are perpendicular to the ultrasound transmitting window cover.

26. The phantom of claim 25 wherein there are two sets of large diameter cylinders with the cylinders in one set having a different backscatter coefficient than the cylinders in the other set and both of which differ from the backscatter coefficient of the background material.

27. The phantom of claim 26 wherein the backscatter coefficient of the large diameter cylinders is selected so that the contrast between the large diameter cylinders and the background material is 3 dB or less.

28. The phantom of claim 25 wherein in the section containing the array of fibers has a backscatter coefficient much lower than that of the tissue-mimicking material in the other sections.

29. The phantom of claim 25 wherein the backscatter coefficient of the spheres in the array of spheres relative to the background material is −35 dB or less, the backscatter coefficient of the large diameter target cylinders relative to the background material is −3.0 dB or less, and the backscatter coefficient of the section containing the array of fibers is −28 dB or less.

30. The phantom of claim 25 wherein the background tissue mimicking material comprises an aqueous mixture of large organic water soluble molecules and a gel forming material.

31. The phantom of claim 30 wherein the background material additionally includes solid scattering particles.

32. The phantom of claim 30 wherein the spheres in the array of spheres and the large and small diameter cylinders are formed of the background material but differing from the background material in components such that at least one of the ultrasonic speed, attenuation coefficient or backscatter coefficient differs from that of the background material.

33. The phantom of claim 25 wherein the phantom container includes a top planar ultrasound transmitting window cover wherein the plane of the array of fibers is perpendicular to the top ultrasound transmitting window cover and wherein the phantom container includes a side planar ultrasound transmitting window cover the plane of which is perpendicular to the plane of the top window cover and parallel to the plane of the array of fibers.

34. The phantom of claim 33 wherein the section containing the array of fibers has a backscatter coefficient much lower than that of the tissue mimicking material in other sections of the phantom.

35. The phantom of claim 25 wherein the section containing the small diameter cylinders has a background material having a much higher attenuation coefficient than the other sections of the phantom.

36. The phantom of claim 35 wherein the attenuation coefficient of the background material in the section containing the small diameter cylinder is at least 0.7 dB/cm/MHz and the attenuation coefficient in the background material in the remaining sections is 0.5 dB/cm/MHz or less.

* * * * *